United States Patent [19]
Kos

[11] Patent Number: 4,827,952
[45] Date of Patent: May 9, 1989

[54] DENTAL FLOSSER AND DENTAL FLOSS

[76] Inventor: Peter Kos, 12 Cavalry Pl., Ridgefield, Conn. 06877

[21] Appl. No.: 114,305

[22] Filed: Oct. 27, 1987

[51] Int. Cl.⁴ ............................................. A61C 15/04
[52] U.S. Cl. ...................................... 132/323; 132/329
[58] Field of Search .................... 132/91, 90, 89, 92 R, 132/93

[56] References Cited

U.S. PATENT DOCUMENTS

| | | | |
|---|---|---|---|
| 788,947 | 5/1905 | Roth | 132/91 |
| 1,171,177 | 2/1916 | Del'eau | 132/92 R |
| 1,815,408 | 7/1931 | Jordan | 132/91 |
| 2,180,522 | 11/1939 | Henne | 132/91 |
| 2,443,415 | 6/1948 | Buscarino | 132/91 |
| 2,650,598 | 9/1953 | Rodesci | 132/91 |
| 3,474,799 | 10/1969 | Cappello | 132/90 |
| 4,016,892 | 1/1977 | Chodorow | 132/91 |
| 4,253,477 | 3/1981 | Eichman | 132/91 |
| 4,304,246 | 12/1981 | Yafai | 132/91 |
| 4,427,018 | 1/1984 | Lagace | 132/91 |
| 4,655,233 | 4/1987 | Laughlin | 132/91 |

Primary Examiner—Paul J. Hirsch
Attorney, Agent, or Firm—St.Onge Steward Johnston & Reens

[57] ABSTRACT

A dental flosser is described wherein a pair of floss-holding arms can be moved in parallel motion so as to enhance the cleaning action of a dental floss. The dental floss is provided with beads that releasably engage the arm ends in tension in a manner so that vigorous action of the dental flosser does not release the floss, yet enables its easy removal after use. The dental flosser is formed of a convenient unitary plastic structure in which movable components are affixed with live hinges. Various beaded dental floss forms are described.

6 Claims, 1 Drawing Sheet

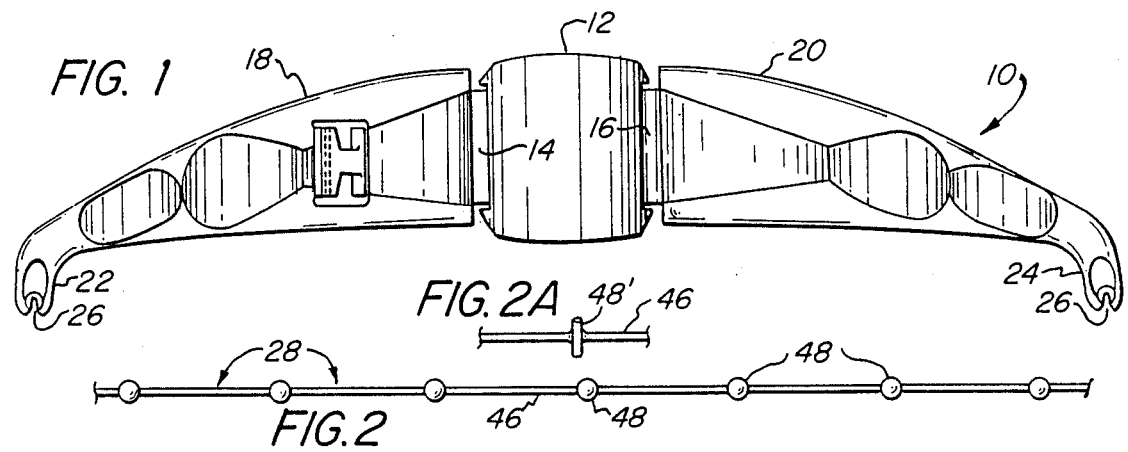
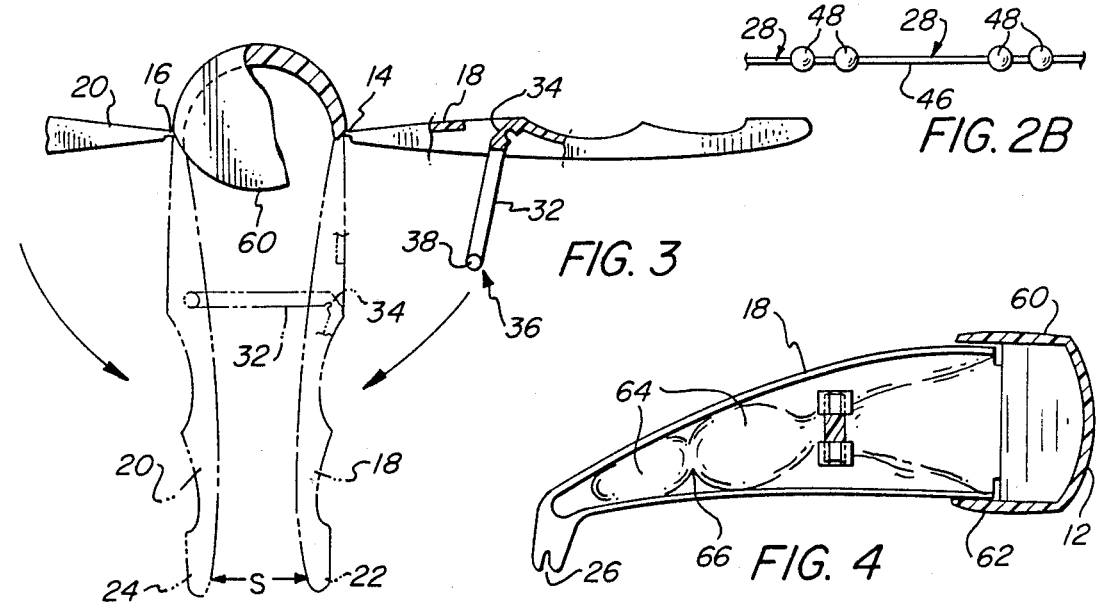
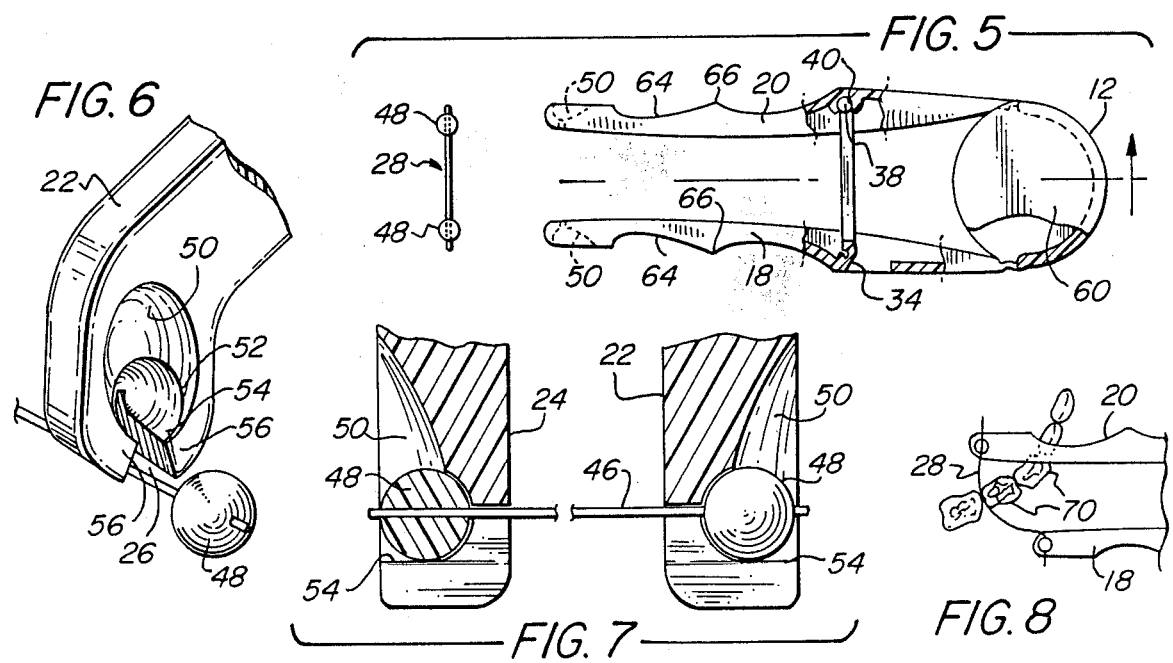

DENTAL FLOSSER AND DENTAL FLOSS

FIELD OF THE INVENTION

This invention relates to a dental flosser and dental floss.

BACKGROUND OF THE INVENTION

Various devices and techniques have been described to make dental flossings so convenient that this type of dental care would become a widespread, generally accepted practice. One technique involves producing small disposable inexpensive dental flossers that are made of plastic and have a small portion of dental floss imbedded at the ends of the arms attached to a tiny handle. U.S. Pat. No. 4,006,750 is exemplary of this type of flosser.

In another flosser, as described and shown in U.S. Pat. No. 1,815,408, a holder is formed of a handle and arms or tines that rigidly extend from the handle. The ends of the arms have small notches that are shaped to capture knots formed in a floss. The distance between the knots is slightly less than that between the notches in the arms so that the floss can be kept sufficiently taut to perform teeth cleaning. Knots on a short length of floss, however, are clumsy to manipulate and insert into the notches and are likely to slip out of the notch during use. In the U.S. Pat. No. 1,815,408 a small length of knotted floss is shown, and this tends to be particularly difficult to handle.

In U.S. Pat. No. 3,799,177 a dental flosser is shown wherein a dental floss is held taut between the ends of generally parallel arms by an adjustable pin placed between the arms. The arms are pivotally mounted at one end to a rocker that pivots about an axis. A lever actuates the rocker to cause the arms to move forward and backward in a generally parallel manner.

These dental flossers appear useful within their particular capabilities, but either are too complex or if simple in construction do not provide a satisfactory utility for teeth cleaning.

SUMMARY OF THE INVENTION

With a dental flosser and dental floss in accordance with the invention, the use of the floss can be effectively applied with a simple structure that facilitates teeth cleaning.

As described herein according to one form of the invention, a dental flosser is provided in which discrete pieces or sections of a particular dental floss are used. The flosser is formed with a hub shaped to comfortably fit in the hand and to which arms are pivotally connected. A cross tie is provided that pivotally attaches to the arms at a location between the ends of the arms and the hub so as to enable the arms to be conveniently moved back and forth. The entire flosser can be formed of a single plastic piece with live hinges between the hub and the arms.

The ends of the arms are provided with slots to receive pieces or sections of a floss carrying beads. The beads fit in recesses at the arm ends so that the floss between beads can be held in tension for teeth cleaning, yet can be conveniently removed after use. The floss can be formed of individual pieces or as a continuous floss thread to which beads of a different or similar material are affixed at regular intervals.

When a dental flosser in accordance with the invention is formed of substantially a single plastic member with live hinges for the movable parts, an inexpensive, conveniently usable device is provided. The use of beaded dental floss segments facilitates the retention of the floss by the flosser during use as well as subsequent removal and disposal.

As further described herein, a beaded dental floss in accordance with the invention is convenient to use in a conventional manual manner by spreading out the distances between successive beads. The beads then form convenient holding places for the user.

It is, therefore, an object of the invention to provide a dental flosser and dental floss that are of simple construction and convenient and effective to use.

These and other others and advantages of the invention can be understood from the following detailed description of several embodiments as shown in the drawings.

BRIEF DESCRIPTION OF DRAWINGS

FIG. 1 is an end view in elevation of a dental flosser in accordance with the invention;

FIG. 2 is a top view of one dental floss in accordance with the invention;

FIG. 2A is a partial top view of another dental floss in accordance with the invention;

FIG. 2B is a partial top view of still another form of a dental floss of this invention;

FIG. 3 is a partial top view of the dental flosser of FIG. 1;

FIG. 4 is a side view in elevation of a folded form of the dental flosser shown in FIG. 1;

FIG. 5 is a top view of the folded dental flosser of FIG. 1 and a dental floss piece in accordance with the invention;

FIG. 6 is an enlarged perspective partial view of an arm end of a flosser and a beaded floss used in accordance with the invention;

FIG. 7 is an enlarged partial section view of the arm ends with a floss segment; and FIG. 8 is a partial top view of the dental flosser during use in cleaning teeth.

DETAILED DESCRIPTION OF DRAWINGS

With reference to the drawings, FIG. 1 shows a dental flosser 10 formed of a unitary plastic piece that can, for example, be made in an injection mold. The dental flosser is formed of a generally central hub 12 connected by way of live hinges 14, 16 to generally like-sized arms 18, 20.

Live hinges 14, 16 are preferred so that the dental flosser can be made entirely in one mold. However, other hinges can be used such as a hinge that uses a pintle or another connecting pivotable element with the arms 18, 20 being separable.

In the view of FIG. 1 the arms 18, 20 are shaped so as to conveniently fit alongside each other as shown in dotted lines in FIG. 3 and in solid lines in FIG. 5. The spacings between arms 18, 20 is selected to conveniently span the gap between teeth for cleaning. Each arm end 22, 24 is provided with a floss receiving slot 26 through which a floss segment such as at 28 in FIG. 2 or in FIG. 5 can be removably mounted. The dental floss segments 28 can be part of a continuous dental floss as shown in FIG. 2 or of individual pieces as shown in FIG. 5.

A cross tie 32 is provided between the hub 12 and the arms ends 22, 24. The cross tie acts as a pivoting connecting member whose length is generally about the same as the distance between hinges 14, 16. Cross tie 32 can be a separate piece, but as shown in FIGS. 1, 3, 4 and 5 is connected at one end by way of a live hinge 34 to arm 18. The other end 36 carries a cylindrically shaped cross element 38 that snap fits for pivot motion into a correspondingly shaped but slightly smaller sized recess 40 in arm 20.

A particularly desirable aspect of the invention is the use of a dental floss that can be conveniently applied, used and then removed from dental flosser 10. For this, a dental floss is provided as shown in FIG. 2. The floss is formed of a conventional floss thread 46 with beads 48 at regular intervals. Beads 48 firmly affix to thread 46 so as to provide anchoring points for dental floss thread 46 when it is applied to arms 18, 20.

As shown in FIG. 6 each arm end 22, 24 has a recess 50 which terminates at a seat surface 52 for beads 48. The recess has a front located retainer edge 54 so as to prevent escape of a bead 48 after a dental floss segment 28 has been applied to arms 18, 20.

Instead of a recess 50, a pair of suitable projections, not shown, could be used on the outer surfaces, such as 56 of arms ends 22, 24 and located on each side of a slot 26.

An advantage of the beaded dental floss 28 is its ease of attachment to arms 18, 20 as well as subsequent removal. For attachment the distance between successive beads is selected so as to require a flexure of the arm ends 22, 24 towards each other to seat the beads 48 on seats 52 with tension of the floss thread 46. The tension should be sufficiently high so as to enable scouring of gaps between teeth without dislodging the beads.

Removal of a dental floss segment 28 can be conveniently carried out by inserting a nail into a recess 50 and lifting against a bead 48, with some or without pressing the arm ends 22, 24 together. Beads 48, therefore, preferably have sufficient size to enable capture in arm ends 22, 24 as well as removal.

Beads 48 are also sufficiently sized to make a strong attachment to floss thread 46. Generally beads 48 are sized so that their main cross sectional dimension along the thread 46 is at least about 1.2mm. Beads 48' may be spherically shaped, at least 1.2mm diameter, or disk shaped as at 48' in FIG. 2A. Beads 48 preferably have a main cross sectional dimension of about 3.0mm and are made of a material that can form a strong attachment to a dental floss thread 46. When the dental floss thread is made of nylon, the beads 48 can also be made of nylon.

One technique for using a dental floss in accordance with the invention involves use of a plurality of individual, separate dental pieces one of which is shown in FIG. 5 and which can be cut from a continuous strand as shown in FIGS. 2 or 2B or separately made. In FIG. 2B, bead segments 28 are separated from each other by both short and long threads 46. The short sections, usually about one eighth of an inch, provide cutting places between segments 28.

In the use of the dental floss segment 28 the effect of the cross tie 32 is relied upon. This in effect transforms the arms 18, 20 as part of a generally parallelogram shaped movable dental flosser. This type of structure enables arm ends 22, 24 to be alternately thrust forward of each other as shown in FIG. 8 for an enhanced cleaning effect of the teeth 70 by the dental floss. During rotation the hub 12 is stopped against the arms 18, 20 to avoid excessive hub rotation.

During such use, the flosser 10 is held in one hand the and hub 12 rolled back and forth to move the arms. The hub 12, therefore, has sufficient rigidity to avoid collapse. This is in part provided by upper and lower caps 60, 62, see FIGS. 3 and 4. The outer surfaces of arms 18, 20 are provided with suitable finger gripping recesses 64 and edges 66.

A dental floss such as shown in FIGS. 2 and 5 can also be conveniently used without adaption to a dental flosser 10. In such case, the dental floss beads 48 are sufficiently separated, for example about three inches, from each other to provide a manual working thread segment where the beads 48 provide convenient holding places.

Having thus described a preferred embodiment in accordance with the invention, its advantages can be appreciaed. Variations can be made without departing from the scope of the invention.

What is claimed is:

1. A dental flosser apparatus comprising:
    a substantially continuous plastic elongate member having a central hub and arms extending from the hub, live hinges connecting the hub with the arms, said hinges being sufficiently flexible to enable a rolling hub action whereby one arm is alternately thrust forward of the other during manual manipulation for teeth cleaning while being sufficiently rigid to resist collapse of the hinges towards each other;
    a rigid connecting member to extend between the arms at a location between the hub and the ends of the arms and to pivotally engage the arms so as to maintain their ends spaced from each other with generally parallel movement of the arms during their thrusting motion, said arm ends being shaped to retain a dental floss between them.

2. The dental flosser as claimed in claim 1 wherein the connecting member has one end affixed to one arm with a live hinge.

3. The dental flosser as claimed in claim 2 wherein the other arm has retainer means to releasably hold another end of the connecting member.

4. The dental flosser as claimed in claim 1 wherein the length of the connecting member is selected so as to substantially form a parallelogram shaped pivoting linkage with the arms and hub.

5. A dental flosser comprising:
    a plastic member having end-located arms and a generally central support for the arms and a pair of hinges pivotally attaching the arms to the support;
    a cross tie for pivotal affixation to the arms at a place between their ends and the hinges, the length of the tie and the distance between the hinges being selected generally the same so as to enable generally parallel movement of the arms; and
    means for retaining dental floss between the ends of the arms.

6. The dental flosser as claimed in claim 5 wherein said means releasably retains dental floss to the ends of the arms.

* * * * *